United States Patent
Govari et al.

(10) Patent No.: US 9,675,416 B2
(45) Date of Patent: Jun. 13, 2017

(54) PREVENTION OF STEAM POPS DURING ABLATION

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US); Joseph Thomas Keyes, Glendora, CA (US); Athanassios Papaioannou, Los Angeles, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 2 days.

(21) Appl. No.: 14/661,307

(22) Filed: Mar. 18, 2015

(65) Prior Publication Data

US 2015/0305812 A1    Oct. 29, 2015

Related U.S. Application Data (60) Provisional application No. 61/984,953, filed on Apr. 28, 2014.

(51) Int. Cl.
*A61B 18/18* (2006.01)
*A61B 18/22* (2006.01)
(Continued)

(52) U.S. Cl.
CPC ............ *A61B 18/22* (2013.01); *A61B 5/0084* (2013.01); *A61B 18/1492* (2013.01); *A61B 18/24* (2013.01); *A61B 5/0422* (2013.01); *A61B 5/6852* (2013.01); *A61B 2017/00066* (2013.01); *A61B 2018/00577* (2013.01); *A61B 2018/00642* (2013.01); *A61B 2018/00666* (2013.01); *A61B 2018/00708* (2013.01); *A61B 2018/00773* (2013.01)

(58) Field of Classification Search
CPC ........ A61B 18/24; A61B 18/22; A61B 18/245
USPC .......................................................... 606/15
See application file for complete search history.

(56) References Cited

U.S. PATENT DOCUMENTS 6,226,542 B1    5/2001    Reisfeld
6,301,496 B1    10/2001    Reisfeld
(Continued)

FOREIGN PATENT DOCUMENTS

WO    WO 2004/028353 A2    4/2004

OTHER PUBLICATIONS

Holmes, Douglas S. et al., Abstract 13330: Steam Pop Prediction and Detection During Radiofrequency Ablation, Circulation, 2011, 124:A13330.
(Continued)

*Primary Examiner* — Daniel Cerioni
(74) *Attorney, Agent, or Firm* — Roberts Mlotkowski Safran Cole & Calderon, P.C.

(57) ABSTRACT

Tissue ablation is carried out using a probe having a distal conductive cap. At least one optical fiber is contained within the probe and terminates in proximity to an outer surface of the conductive cap. The optical fiber conveys optical radiation to the tissue while the power generator is activated and receives reflected optical radiation. An optical module measures the received reflected optical radiation, and a processor linked to the optical module analyzes the reflected optical radiation to determine impending steam pop events.

9 Claims, 8 Drawing Sheets

(51) Int. Cl.
    *A61B 18/24*     (2006.01)
    *A61B 18/14*     (2006.01)
    *A61B 18/00*     (2006.01)
    *A61B 17/00*     (2006.01)
    *A61B 5/00*     (2006.01)
    *A61B 5/042*     (2006.01)

(56) References Cited

U.S. PATENT DOCUMENTS

| | | |
|---|---|---|
| 6,332,089 B1 | 12/2001 | Acker et al. |
| 6,522,930 B1* | 2/2003 | Schaer ............... A61B 18/1492 606/41 |
| 6,618,612 B1 | 9/2003 | Acker et al. |
| 6,690,963 B2 | 2/2004 | Ben-Haim et al. |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 8,147,484 B2 | 4/2012 | Lieber et al. |
| 8,641,706 B2 | 2/2014 | Lieber et al. |
| 2004/0068178 A1 | 4/2004 | Govari |
| 2004/0102769 A1 | 5/2004 | Schwartz et al. |
| 2004/0147920 A1 | 7/2004 | Keidar |
| 2006/0122587 A1* | 6/2006 | Sharareh ............ A61B 18/22 606/11 |
| 2006/0229515 A1* | 10/2006 | Sharareh ............ A61B 5/0075 600/476 |
| 2008/0097220 A1 | 4/2008 | Lieber et al. |
| 2011/0130648 A1 | 6/2011 | Beeckler et al. |
| 2012/0245572 A1* | 9/2012 | Lieber ............ A61B 5/0084 606/10 |
| 2012/0265184 A1 | 10/2012 | Sliwa et al. |
| 2014/0171936 A1 | 6/2014 | Govari et al. |

OTHER PUBLICATIONS

Kotini, Pavitra et al., Detection of microbubble formation during radiofrequency ablation using phonocardiography, European Society of Cardiology®, Europace, Feb. 12, 2006, pp. 333-335, vol. 8, Issue 5.

* cited by examiner

PREVENTION OF STEAM POPS DURING ABLATION

CROSS-REFERENCE TO RELATED APPLICATIONS

This application claims the benefit of U.S. Provisional Application No. 61/984,953, which is herein incorporated by reference.

BACKGROUND OF THE INVENTION

1. Field of the Invention

This invention relates to invasive medical devices. More particularly, this invention relates to ablation of tissue using such devices.

2. Description of the Related Art

Ablation of body tissue using electrical energy is known in the art. The ablation is typically performed by applying alternating currents, for example radiofrequency energy, to the electrodes, at a sufficient power to destroy target tissue. Typically, the electrodes are mounted on the distal tip of a catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects, coagulum, and or explosive steam pops due to overheating. Such overheated areas can develop high impedance, and may form a functional barrier to the passage of heat. The use of slower heating provides better control of the ablation, but unduly prolongs the procedure.

Steam pops or microbubble formation can occur during RF ablation when tissue temperatures exceed 100 C. While tactile and audible cues are used for their detection, background lab noise and catheter movement may confound identification. Steam pops are particularly hazardous. For example, during RF ablation, steam pops caused by tissue overheating may result in cardiac perforation. The present disclosure deals with recognition of impending steam pops in time to take corrective action, e.g., controlling the power output of the ablator.

Previous attempts to recognize steam pops include the use of phonocardiography. For example, the document *Detection of microbubble formation during radiofrequency ablation using phonocardiography*, Kotini et al., EP Europace Volume 8, Issue 5 Pp. 333-335 proposes detection of characteristic signatures prior to steam pops using a computer-based phonocardiography system.

In another approach, the document *Steam Pop Prediction and Detection During Radiofrequency Ablation*, Holmes et al., Circulation 2011 124:A13330 describes an Electrical Coupling Index (ECI), in which resistive and reactive impedance between the ablation catheter and tissue. The ECI was displayed as a continuous waveform during ablation. A steam pop prediction algorithm is said to have predicted 92% of all steam pops at least 3 seconds before they occurred. The negative predictive value of the steam pop prediction algorithm is stated as 98%.

U.S. Pat. No. 8,147,484 to Lieber et al. discloses real-time optical measurements of tissue reflection spectral characteristics while performing ablation. The technique involves the radiation of tissue and recapturing of light from the tissue to monitor changes in the reflected optical intensity as an indicator of steam formation in the tissue for prevention of steam pop. Observation is made to determine whether measured reflectance spectral intensity (MRSI) increases in a specified time period followed by a decrease at a specified rate in the MRSI. If there is a decrease in the MRSI within a specified time and at a specified rate, then formation of a steam pocket is inferred.

SUMMARY OF THE INVENTION

According to disclosed embodiments of the invention, high frequency fluctuations in optical reflectivity measured by optical sensors near the tip of a catheter predict an imminent occurrence of steam pops, i.e., within a few seconds. Without being bound by any particular theory, the following discussion is offered to facilitate understanding of the invention: a possible reason for this phenomenon relates to optical properties of a developing steam pocket or microbubbles within the target tissue.

There is provided according to embodiments of the invention an apparatus, including a power generator of ablative electrical energy and an insertion tube configured for insertion into proximity with tissue in a body of a patient. The insertion tube has an electrical conductor for conveying the ablative electrical energy to the tissue, a conductive cap attached to the distal end of the insertion tube and coupled electrically to the electrical conductor, and at least one optical fiber terminating in proximity to an outer surface of the conductive cap. The optical fiber conveys optical radiation to the tissue while the power generator is activated and receives reflected optical radiation. An optical module measures the received reflected optical radiation, and a processor linked to the optical module analyzes the reflected optical radiation.

According to an aspect of the apparatus, analyzing the reflected optical radiation includes recognizing a characteristic signature in the reflected optical radiation indicative of an impending steam pop event.

According to another aspect of the apparatus, the characteristic signature comprises a high frequency pattern in a second derivative of the reflected optical radiation with respect to time.

According to one aspect of the apparatus, the processor is configured for recognizing the high frequency pattern by performing a Fourier transform on the second derivative thereof and identifying spectral peaks exceeding 0.5 Hz in a spectrum of the Fourier transform.

According to a further aspect of the apparatus, the processor is configured for obtaining additional reflected optical radiation when the ablation power generator is deactivated, performing an additional Fourier transform on the second derivative of the additional reflected optical radiation and subtracting the additional Fourier transform from the Fourier transform.

There is further provided according to embodiments of the invention a method that is carried out by the above-described apparatus.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Figure 1:
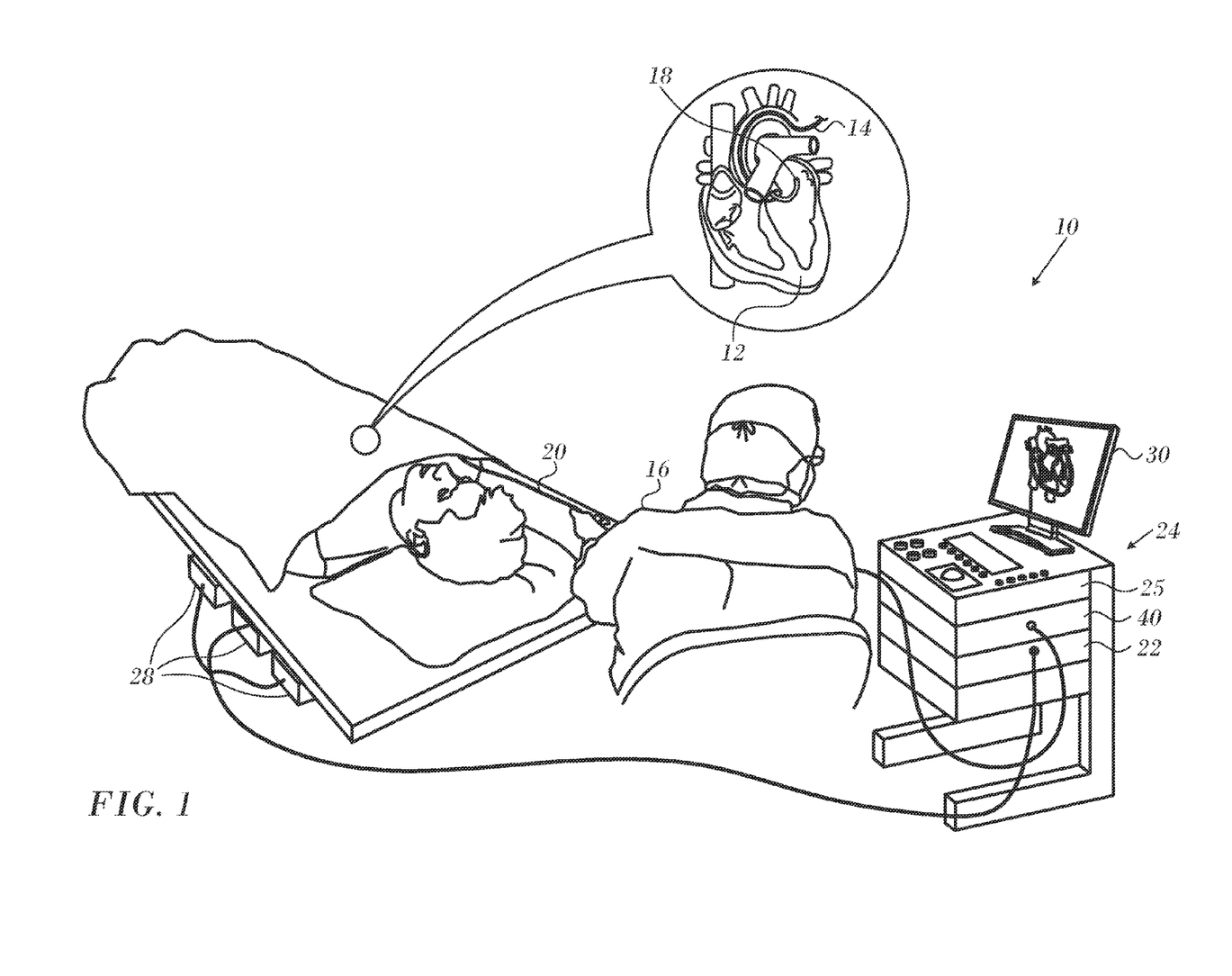
FIG. 1 is a pictorial illustration of a system for performing ablative procedures, which is constructed and operative in accordance with a disclosed embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart. The operator 16, who is typically a physician, brings the catheter's distal tip 18 into contact with the heart wall at an ablation target site. Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. Although the embodiment described with respect to FIG. 1 is concerned primarily with cardiac ablation; the principles of the invention may be applied, mutatis mutandis, to other catheters and probes and to body tissues other than the heart.

Areas determined to be abnormal by evaluation of the electrical activation maps can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 60° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention can be applied to different heart chambers, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24. The console 24 typically contains an ablation power generator 25. The catheter 14 may be adapted to conduct ablative energy to the heart using any known ablation technique, e.g., radiofrequency energy, ultrasound energy, and laser energy. Such methods are disclosed in commonly assigned U.S. Pat. Nos. 6,814,733, 6,997,924, and 7,156,816, which are herein incorporated by reference.

The positioning processor 22 is an element of a positioning subsystem of the system 10 that measures location and orientation coordinates of the catheter 14.

In one embodiment, the positioning sub-system comprises a magnetic position tracking arrangement that determines the position and orientation of the catheter 14 by generating magnetic fields in a predefined working volume its vicinity and sensing these fields at the catheter. The magnetic position tracking arrangement typically comprises a set of external radiators, such as field generating coils 28, which are located in fixed, known positions external to the patient. The field generating coils 28 are driven by field generators (not shown), which are typically located in the console 24, and generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking techniques that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning sub-system shown in FIG. 1 uses magnetic fields, the methods described below may be implemented using any other suitable positioning system, such as systems based on electromagnetic fields, acoustic or ultrasonic measurements.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 30. The signal processing circuits typically receive, amplify, filter and digitize signals from the catheter 14, including signals generated by the above-noted sensors and a plurality of sensing electrodes (not shown) located distally in the catheter 14. The digitized signals are received and used by the console 24 to compute the position and orientation of the catheter 14 and to analyze the electrical signals from the electrodes. The information derived from this analysis may be used to generate an electrophysiological map of at least a portion of the heart 12 or structures such as the pulmonary venous ostia, for diagnostic purposes such as locating an arrhythmogenic area in the heart or to facilitate therapeutic ablation.

An optical module 40 provides optical radiation, typically from, but not limited to, a laser, an incandescent lamp, an arc lamp, or a light emitting diode (LED), for transmission from distal tip 18 to the target tissue. The module receives and analyzes optical radiation returning from the target tissue and acquired at the distal end, as described below.

Typically, the system 10 includes other elements, which are not shown in FIG. 1 for the sake of simplicity. For example, the system 10 may include an electrocardiogram (ECG) monitor, coupled to receive signals from one or more body surface electrodes, to provide an ECG synchronization signal to the console 24. The system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

One system that embodies the above-described features of the system 10 is the CARTO® 3 System, available from Biosense Webster, Inc., 3333 Diamond Canyon Road, Diamond Bar, Calif. 91765. This system may be modified by those skilled in the art to embody the principles of the invention described herein.

Some embodiments of the present invention that are described hereinbelow provide irrigated ablation electrodes with fiberoptic elements and optional embedded temperature sensors that provide accurate tissue temperature assessment. Such electrodes typically comprise a conductive cap, which is attached to the distal tip 18 (FIG. 1) of the catheter 14. A cooling fluid flows out through an array of perforations in the electrode to irrigate the tissue under treatment. Further details of these embodiments are disclosed in commonly assigned application Ser. No. 14/090,614 entitled Irrigated Catheter Tip with Temperature Sensor and Optic Fiber Arrays, which is herein incorporated by reference.

Figure 2:
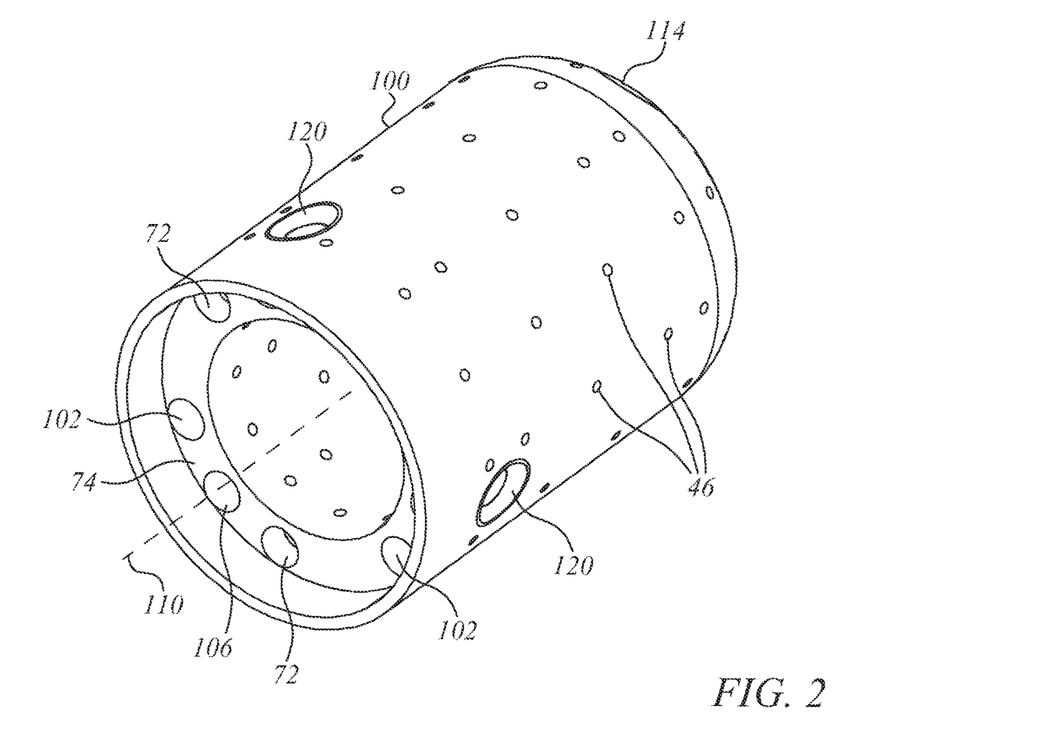
FIG. 2 is a schematic, perspective illustration of a catheter cap in accordance with an embodiment of the invention.

Reference is now made to FIG. 2, which is a schematic, perspective illustration of a catheter cap 100, in accordance with an embodiment of the invention. Cap 100 comprises a side wall 74 that is on the order of 0.4 mm thick, in order to provide the desired thermal insulation between optional temperature sensors 48 and the irrigation fluid inside a central cavity 76 of the tip. Irrigation fluid exits cavity 76 through apertures 46.

Figure 3:
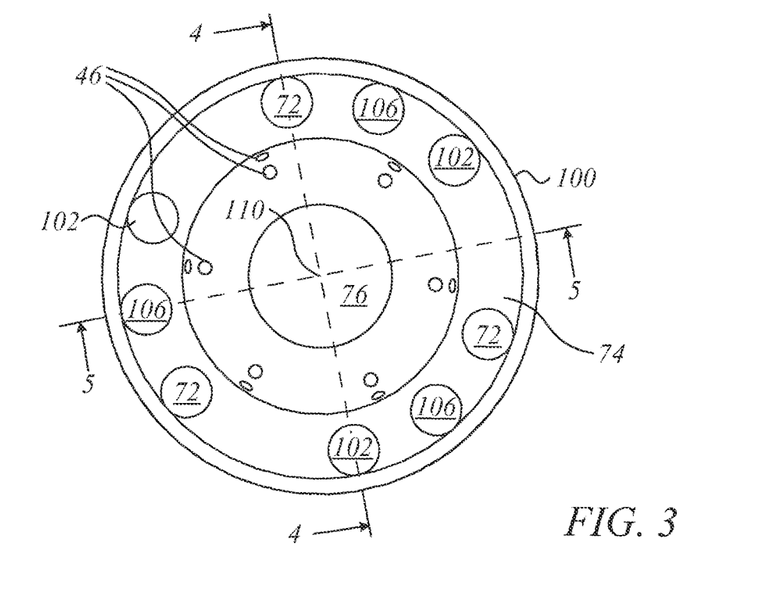
FIG. 3 is a schematic end view showing the interior of the cap shown in FIG. 2, in accordance with an embodiment of the invention.
Figure 4:
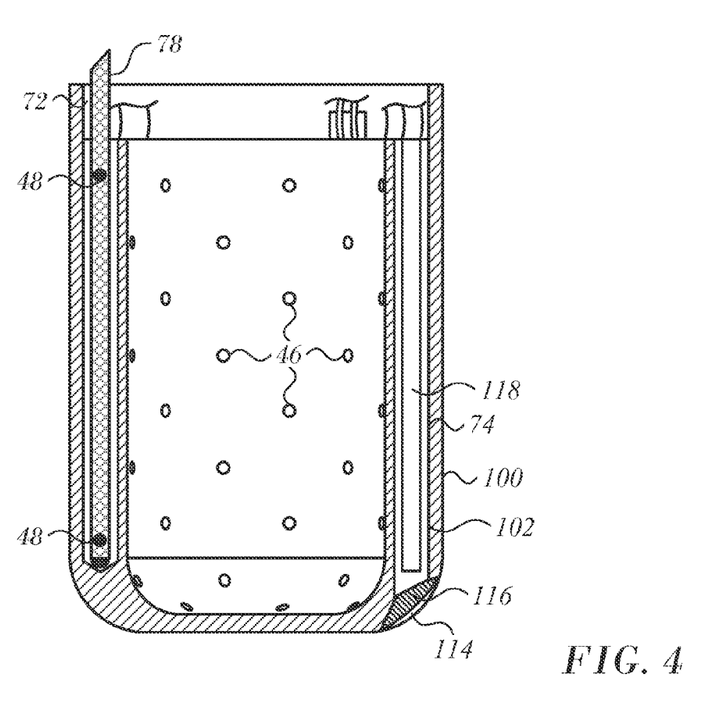
FIG. 4 is a schematic sectional view taken along line 4-4 of FIG. 3, in accordance with an embodiment of the invention.

Reference is now made to FIG. 3, which is a schematic end view showing the interior of the cap 100, in accordance with an embodiment of the invention. Reference is also made to FIG. 4 and to FIG. 5, which are schematic sectional views taken respectively along the lines 4-4 and 5-5 of FIG. 3, in accordance with an embodiment of the invention. Three through longitudinal bores 102 and three blind longitudinal bores 106 are formed in side wall 74. As shown in FIG. 3, the three sets of bores 72, 102, 106 may be distributed symmetrically around an axis 110 of cap 100. However, the bores are not necessarily distributed symmetrically around axis 110. Optional sensors 48 are mounted in hollow tubes 78, which are filled with a suitable glue, such as epoxy and fitted into longitudinal bores 72 in side wall 74. Tubes 78 may comprise a suitable plastic material, such as polyimide, and may be held in place by a suitable glue, such as epoxy. This arrangement provides an array of six sensors 48, with possible advantages of greater ease of manufacture and durability.

As best seen in FIG. 4, each through longitudinal bore 102 terminates in an opening 114 in the outer surface of wall 74, and a transparent window 116 is placed in the opening. A fiber optic 118 is inserted into each of the through bores. In some embodiments, temperature sensors 48 may not be installed in wall 74, and only fiber optics 118 are incorporated into the wall. Such an embodiment enables determination of tissue contact with the cap, and/or characterization of the tissue in proximity to the cap, by methods described below.

Figure 5:
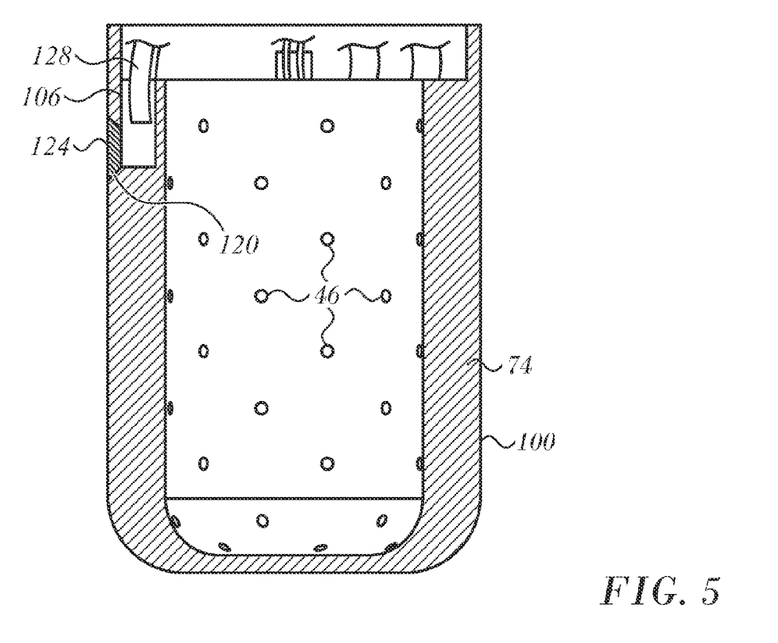
FIG. 5 is a schematic sectional view taken along line 5-5 of FIG. 3, in accordance with an embodiment of the invention.

As best seem in FIG. 5, there is a respective opening 120, in the outer surface of wall 74, to each blind bore 106, and a transparent window 124 is placed in each opening 120. A fiber optic 128 is inserted into each of the blind bores. Windows 116, 124 act as seals preventing fluid external to the outer surface of cap 100 from penetrating into the bores containing the fiber optics. Windows 116, 124 may be formed by filling openings 114, 120 with an optically transparent glue or epoxy. In some embodiments, the material of the windows may be filled with a scattering agent to diffuse light passing through the windows.

Alternatively, the windows may be formed from an optical quality flat or lensed material, and may be secured to their openings with glue.

In one embodiment, each fiber optic 118 or each fiber optic 128 is a single fiber optic, typically having a diameter of approximately 175 μm. In an alternative embodiment each fiber optic 118 or each fiber optic 128 comprises a bundle of substantially similar fiber optics, typically having a bundle diameter also of approximately 175 μm. Implementing the fiber optics as bundles increases the flexibility of cap 100 with respect to more proximal regions of the catheter 14 (FIG. 1).

Such an increase in flexibility is advantageous if cap 100 is connected to the more proximal regions of the catheter by a spring whose deflections are measured for the purpose of measuring a force on the cap, since the increased flexibility means there is little or no change in the spring deflection for a given force. A spring that may be used to join the cap 100 to the more proximal regions of the catheter is described in U.S. patent application Ser. No. 12/627,327, to Beeckler et al., whose disclosure is incorporated herein by reference.

Optical module 40 (FIG. 1) is configured to be able to provide optical radiation to any one of fiber optics 118 and 128, for transmission from any of the associated windows 116, 124 in order to irradiate tissue in proximity to cap 100. Simultaneously, the optical module 40 is able to acquire, via any or all of the windows, radiation returning from the irradiated tissue.

The array of windows 116, 124, and their associated fiber optics, enables embodiments of the present invention to employ a number of different methods, using optical radiation, for determining characteristics of the irradiated tissue, as well as the proximity of cap 100, or a region of the cap, with respect to the tissue. By way of example, three such methods are described below, but those having ordinary skill in the art will be aware of other methods, and all such methods are included within the scope of the present invention.

A first method detects contact of any one of windows 116, 124, and consequently of the catheter, with tissue. Optical radiation of known intensity is transmitted through each fiber optic, so as to exit from the optic's window. The intensity of the radiation returning to the window is measured while cap 100 is not in contact with tissue, typically while the cap is in the blood of heart 12 (FIG. 1). Optical module 40 may use these intensities as reference values of the optical radiation.

For any given window, a change in the value from the window's reference value, as measured by the module, may be taken to indicate that the window is in contact with tissue.

Figure 6:
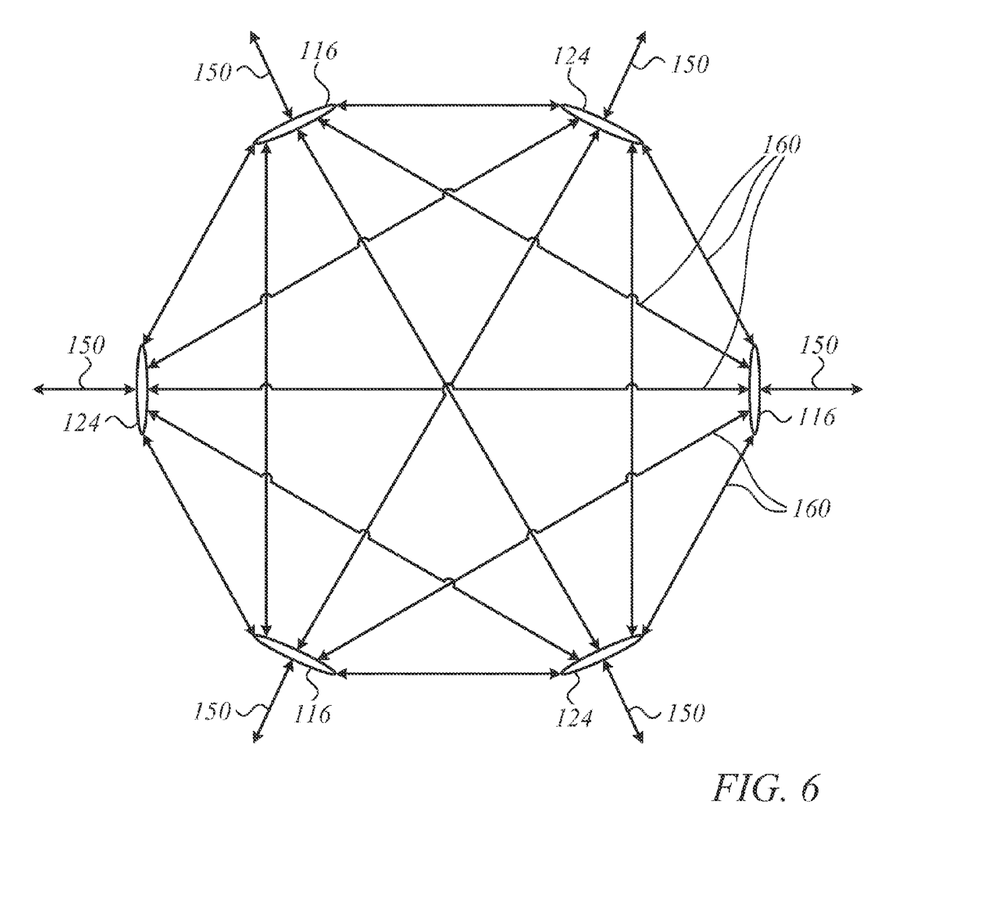
FIG. 6 schematically illustrates paths taken by light to/from windows in the cap shown in FIG. 2, in accordance with an embodiment of the invention.

A second method measures characteristics of tissue being irradiated by the optical radiation. Reference is now made to FIG. 6, which schematically illustrates paths taken by light to/from windows in the cap 100 (FIG. 2), in accordance with an embodiment of the invention.

As illustrated in FIG. 6, for all six windows 116, 124 there are a total of 21 different paths, comprising 6 paths 150 where radiation from a given window returns to that window, and 15 paths 160 where radiation from a given window returns to a different window. The change of optical radiation for a given path or group of paths depends on characteristics of tissue in the path or group of paths, so that measurements of the change in all of the paths provide information related to characteristics of the tissue in proximity to cap 100.

For example, the change in all of the paths may be measured by sequentially transmitting, in a time multiplexed manner, optical radiation from each of the windows 116, 124, and measuring the returning radiation. A first transmission from a first window in such a sequence provides values for five paths 160 plus a return path 150 to the first window. A second transmission from a second window provides values for four new paths 160 plus return path 150 to the second window. A third transmission from a third window provides values for three new paths 160 plus return path 150 to the third window. A fourth transmission from a fourth window provides values for two new paths 160 plus return path 150 to the fourth window. A fifth transmission from a fifth window provides values for one new path 160 to the sixth window, and return path 150 to the fifth window). A sixth and final transmission from a sixth window provides one return path 150 through the sixth window.

Optical module 40 (FIG. 1) may measure the changes of all the paths, and, using a calibration procedure, may derive from the changes optical characteristics of tissue within the paths. Such characteristics may include an overall level of ablation of tissue, or an amount and/or type of necrotic tissue, in the paths or the characteristic signature indicative of impending steam pop events described below.

A third method uses changes of levels of optical radiation returning to either or both windows 116, 124, such as are described in the two methods, to make an estimate of the wall thickness of tissue being illuminated by the optical radiation.

Although a number of particular implementation examples have been shown and described above, alternative implementations of the principles embodied in these examples will be apparent to those skilled in the art after reading the foregoing description and are considered to be within the scope of the present invention.

EXAMPLES

Examination of reflectance data (intensity with respect to time) indicates that 668.7 nm showed the largest difference between steam pop events and situations in which steam pops did not occur. In the following examples, the graphs on the left side of the figure show intensity over time at 668.7 nm. Time is arbitrary on the scale. However, the data is representative of a 60-second ablation performed at random powers and forces, with 5 seconds of data recorded postablation. The graphs at the right side of the following figures show the second derivative ($d^2I/dt^2$) of the reflectance data over time.

Figure 7:
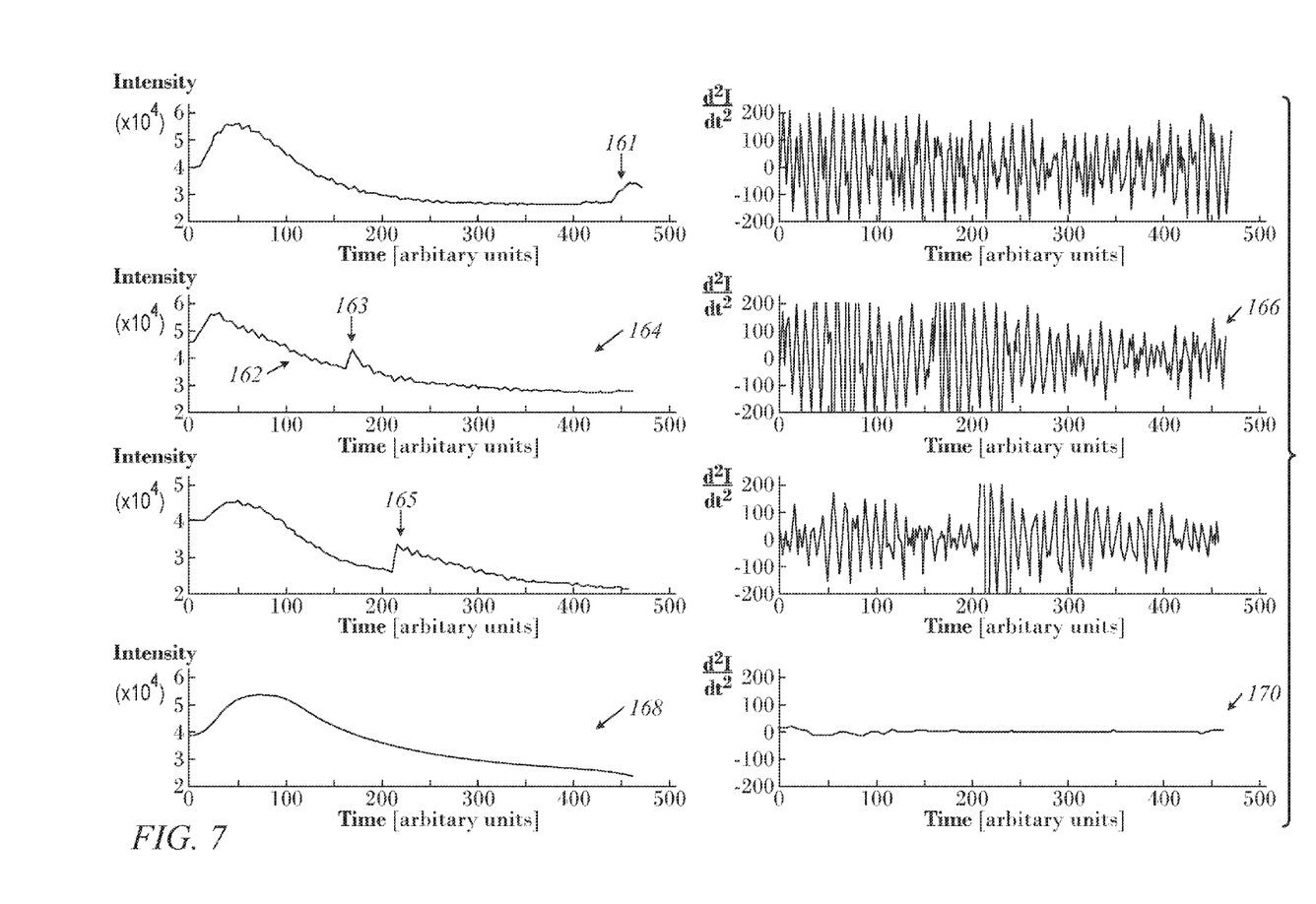
FIG. 7 is a group of four exemplary tracings of reflectance data in accordance with an embodiment of the invention.

Reference is now made to FIG. 7, which is a group of four exemplary tracings of reflectance data in accordance with an embodiment of the invention. Intensity was tuned by increasing binning (8) and integration (100 ms) to maximize the dynamic range. In the upper three tracings, undulations in signal were evident, for example in the region indicated by arrow 162 in tracing 164. In these three tracings, steam pop events were indicated by arrows 161, 163, 165. There are marked fluctuations in the corresponding tracing 166 of the second derivative, Steam pop prediction was highly correlated with a high frequency signal (exceeding 0.5 Hz) for $d^2I/dt^2$. In contrast, the lowermost set of tracings 168, 170 describes an ablation in which no steam pop occurred. It is evident that the signal fluctuations precede the steam pop event.

Figure 8:
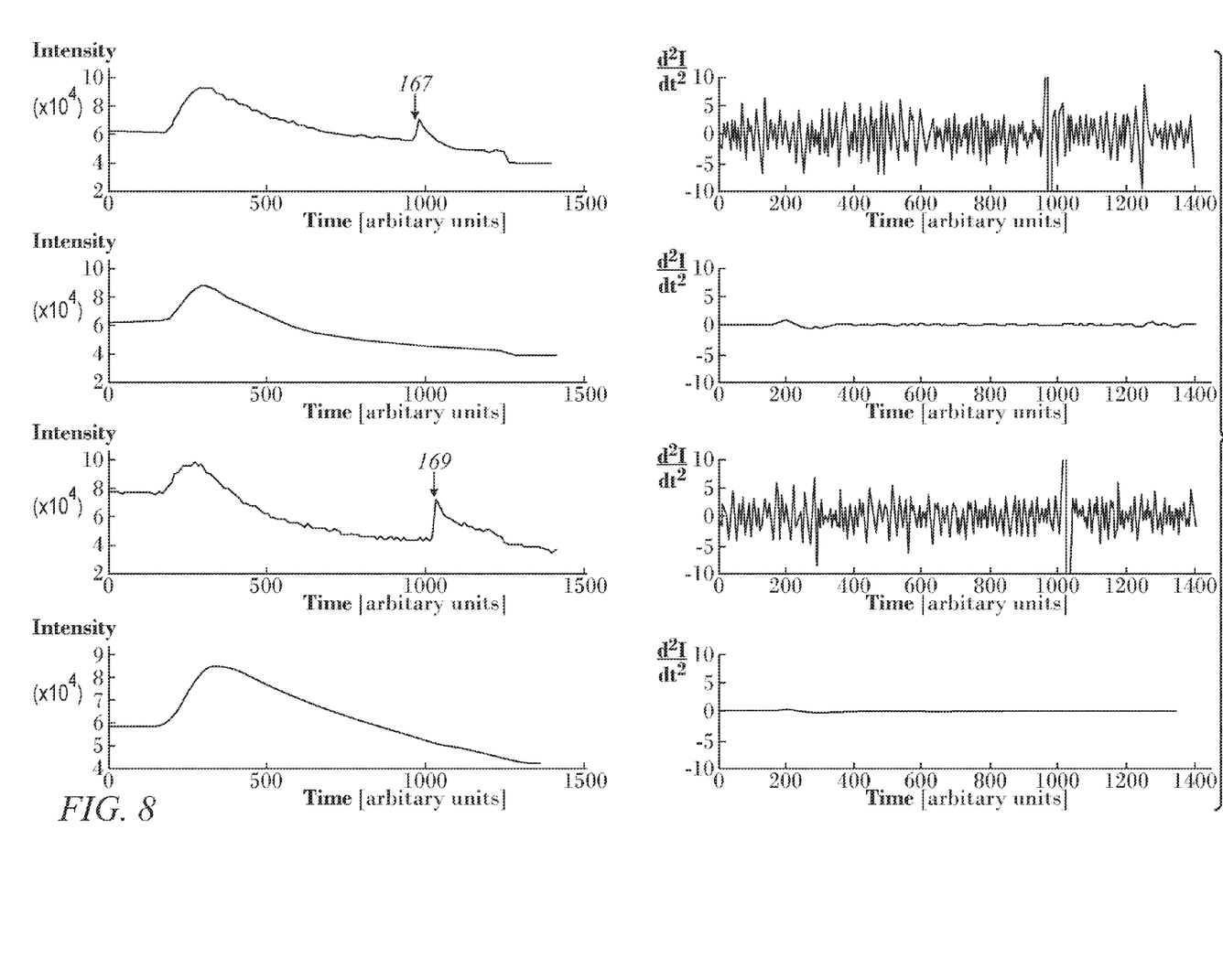
FIG. 8 is a group of four exemplary tracings of reflectance data in accordance with an embodiment of the invention.

Reference is now made to FIG. 8, which is a group of four exemplary tracings of reflectance data in accordance with an embodiment of the invention. In this series, intensity was tuned to get usable signal with short integration (30 ms) and as little binning at possible for lesion-assessment testing. Undulations in signal were less evident but still appeared with the second derivative. Steam pop events were indicated by arrows 167, 169. Steam pop prediction was highly correlated with high frequency signal for $d^2I/dt^2$.

Figure 9:
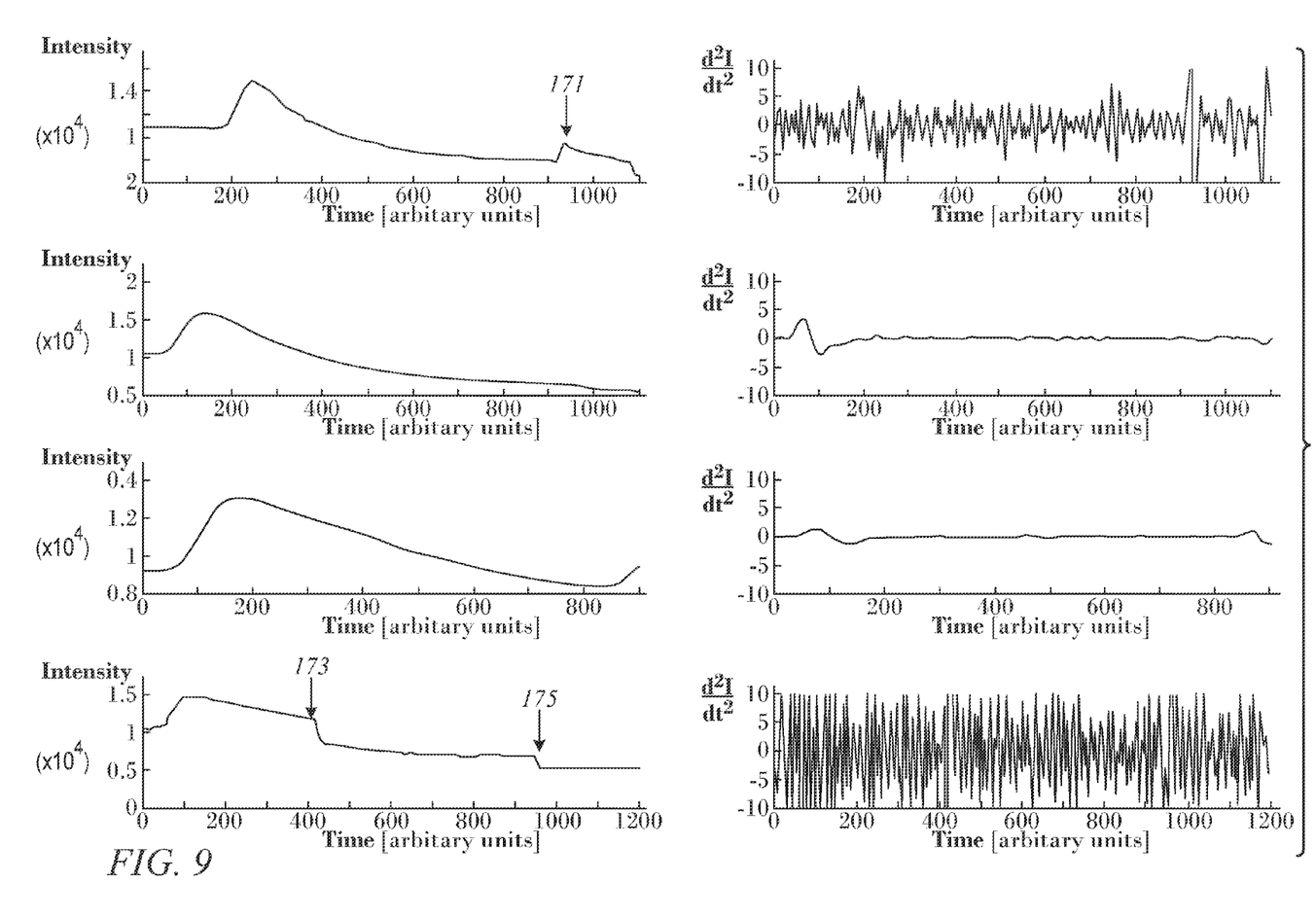
FIG. 9 is a group of four exemplary tracings of reflectance data in accordance with an embodiment of the invention.

Reference is now made to FIG. 9, which is a group of four exemplary tracings of reflectance data in accordance with an embodiment of the invention. Intensity was tuned to get a usable signal with a short integration (10 ms) and as little binning at possible for lesion-assessment testing. Undulations in signal were less evident than on the preceding figures, but still appeared together with a chaotic appearance of the second derivative tracings. Steam pop events were indicated by arrows 171, 173, 175. Steam pop prediction had less correlation (~79%) with the high frequency signal for $d^2I/dt^2$ than that of the previous examples.

Conversion to Frequency Domain.

Figure 10:
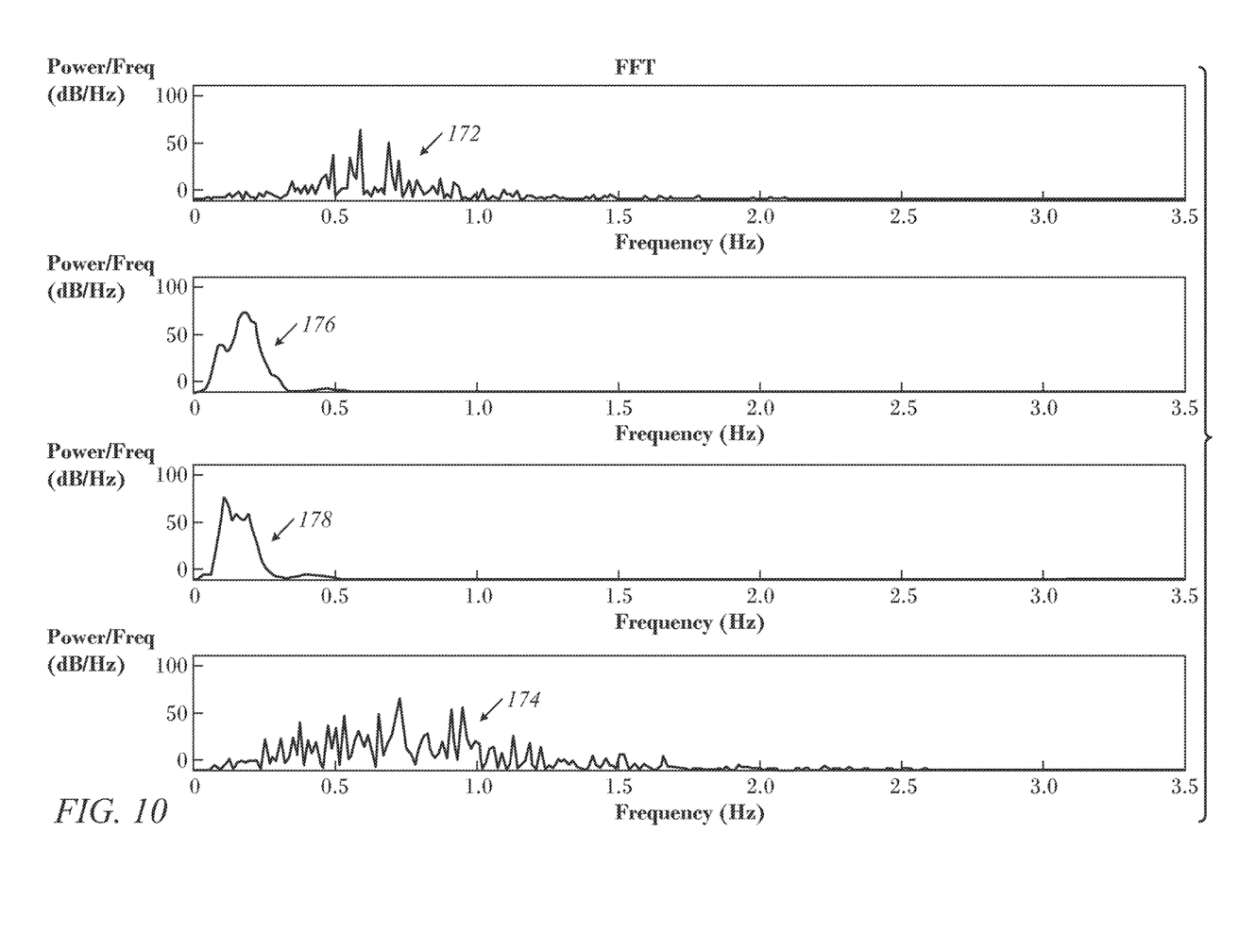
FIG. 10 illustrates FFT plots of the second derivative tracings shown in FIG. 9, in accordance with an embodiment of the invention.

Converting the time-based tracings shown in FIGS. 7-9 to the frequency domain using a Fourier transfer technique, e.g., a Fast Fourier Transform (FFT) technique, reveals characteristic spectra indicative of an impending steam pop. Reference is now made to FIG. 10, which illustrates FFT plots of the second derivative tracings shown at the right side of FIG. 9, in accordance with an embodiment of the invention. Graphs 172, 174 illustrate high frequency spectral peaks indicative of impending steam pop events. Peaks having frequencies exceeding 0.5 Hz are significant. Graphs 176, 178 show a low frequency spectral pattern (less than 0.5 Hz), indicating that steam pop events are not imminent. It is conjectured that the high frequency events correlate with formation of microbubbles in the tissue, followed by their movement and collapse within the top layer of the tissue. When enough microbubbles are present, they can conglomerate and form one large bubble that can rupture (pop) and perforate the tissue.

Evaluating the FFT is useful as it can differentiate between fluctuations in optical intensity resulting from changes in contact force between the catheter and the ablation site and those caused by microbubbles.

It is desirable to perform an FFT on a reflectance reading obtained while ablation is not occurring, e.g., prior to initiation of ablation. A 5-10 second window for this reading is satisfactory. Then the pre-ablation spectrum is subtracted from the FFT obtained during the ablation procedure. It is assumed that catheter movement during the 5-10 second window is representative of catheter movement during ablation. The subtraction procedure largely eliminates artifact due to catheter movement.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. An apparatus, comprising:
    an ablation power generator of ablative electrical energy;
    an insertion tube having a distal end configured for insertion into proximity with tissue in a body of a patient, the insertion tube defining a lumen having disposed therein an electrical conductor for conveying the ablative electrical energy to the tissue;
    a conductive cap attached to the distal end of the insertion tube and coupled electrically to the electrical conductor;
    at least one optical fiber contained within the insertion tube and terminating in proximity to an outer surface of the conductive cap, the at least one optical fiber being configured to
        convey optical radiation to the tissue while the ablation power generator is activated and electrical energy is conveyed to the tissue, and
        receive reflected optical radiation via the at least one optical fiber;
    an optical module configured to provide optical radiation to the at least one optical fiber and to measure the received reflected optical radiation;
    a processor linked to the optical module and configured to analyze the reflected optical radiation in order to recognize a characteristic signature in the reflected optical radiation indicative of an impending steam pop event;
    wherein the characteristic signature comprises a high frequency pattern in a second derivative of the reflected optical radiation with respect to time.

2. The apparatus according to claim 1, wherein the processor is configured for recognizing the high frequency pattern by performing a Fourier transform on the second derivative thereof and identifying spectral peaks in a spectrum of the Fourier transform.

3. The apparatus according to claim 2, wherein the spectral peaks occur at frequencies in the spectrum that exceed 0.5 Hz.

4. The apparatus according to claim 2, wherein the processor is configured for obtaining additional reflected optical radiation when the ablation power generator is deactivated, performing an additional Fourier transform on the second derivative of the additional reflected optical radiation and subtracting the additional Fourier transform from the Fourier transform.

5. A method, comprising the steps of:
    transmitting ablative electrical energy to tissue in a body of a living subject through an insertion tube having a distal end configured for insertion into proximity with the tissue, the insertion tube defining a lumen having disposed therein an electrical conductor for conveying the ablative electrical energy to the tissue, the insertion tube comprising a conductive cap attached to the distal end of the insertion tube and coupled electrically to the electrical conductor;
    conveying optical radiation to the tissue through at least one optical fiber terminating in proximity to an outer surface of the conductive cap while conveying the ablative electrical energy to the tissue;
    receiving reflected optical radiation via the at least one optical fiber; and
    recognizing a characteristic signature in the reflected optical radiation indicative of an impending steam pop event, the characteristic signature comprising a high frequency pattern in a second derivative of the reflected optical radiation with respect to time.

6. The method according to claim 5, further comprising recognizing the characteristic signature by performing a Fourier transform on the second derivative of the received reflected optical radiation and identifying spectral peaks in a spectrum of the Fourier transform.

7. The method according to claim 6, wherein the spectral peaks occur at frequencies in the spectrum that exceed 0.5 Hz.

8. The method according to claim 6, further comprising receiving additional reflected optical radiation when the ablative electrical energy is not being transmitted to the tissue, performing an additional Fourier transform on the second derivative of the additional reflected optical radiation and subtracting the additional Fourier transform from the Fourier transform.

9. A method, comprising:
    providing the apparatus of claim 1;
    transmitting ablative electrical energy to the tissue in the body of a living subject through the distal end of the insertion tube;
    conveying optical radiation to the tissue through the at least one optical fiber terminating in proximity to an outer surface of the conductive cap while conveying the ablative electrical energy to the tissue;
    receiving reflected optical radiation via the at least one optical fiber; and
    recognizing a characteristic signature in the reflected optical radiation indicative of an impending steam pop event.

* * * * *